United States Patent
Ataie et al.

(10) Patent No.: US 9,625,351 B2
(45) Date of Patent: Apr. 18, 2017

(54) COHERENT DUAL PARAMETRIC FREQUENCY COMB FOR ULTRAFAST CHROMATIC DISPERSION MEASUREMENT IN AN OPTICAL TRANSMISSION LINK

(71) Applicant: The Regents of the University of California, Oakland, CA (US)

(72) Inventors: Vahid Ataie, San Diego, CA (US); Ping Piu Kuo, San Diego, CA (US); Stojan Radic, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 37 days.

(21) Appl. No.: 14/198,581

(22) Filed: Mar. 5, 2014

(65) Prior Publication Data

US 2014/0253915 A1    Sep. 11, 2014

Related U.S. Application Data

(60) Provisional application No. 61/773,097, filed on Mar. 5, 2013.

(51) Int. Cl.
*G01M 11/02* (2006.01)
*G01M 11/00* (2006.01)
*H04B 10/079* (2013.01)
*G01N 21/41* (2006.01)

(52) U.S. Cl.
CPC ........ *G01M 11/338* (2013.01); *G01M 11/333* (2013.01); *G01N 21/41* (2013.01); *H04B 10/07951* (2013.01)

(58) Field of Classification Search
CPC ............ G01M 11/338; G01M 11/333; G01M 11/3127; G01M 11/335; H04B 10/07; H04B 10/07951; G01N 21/55; G01N 21/41

See application file for complete search history.

(56) References Cited

U.S. PATENT DOCUMENTS

| | | | |
|---|---|---|---|
| 6,088,088 A | * | 7/2000 | Fortenberry ................. 356/73.1 |
| 6,323,950 B1 | | 11/2001 | Zhang et al. |
| 6,912,359 B2 | | 6/2005 | Blumenthal et al. |
| 6,965,738 B2 | | 11/2005 | Eiselt et al. |

(Continued)

OTHER PUBLICATIONS

Ian Coddington, Coherent Multiheterodyne Spectroscopy Using Stabilized Optical Frequency Combs, Jan. 2, 2008, Physical Review Letters, pp. 1-4.*

(Continued)

*Primary Examiner* — Michael P Lapage
(74) *Attorney, Agent, or Firm* — Eleanor Musick; Musick Davison LLP

(57) ABSTRACT

A wide-band optical frequency comb is provided to estimate an optical phase shift induced in a dispersive material. In contrast to the conventional techniques that rely on a single tunable laser for extracting the dispersion parameter at different frequencies, the wide-band optical frequency comb uses multiple comb lines for simultaneously evaluating the dispersion induced phase shifts in different frequencies. Since the frequency response of the dispersive material is a phase function, a phase associated with each comb line passed through the material represents a discrete measure of the material frequency response.

13 Claims, 3 Drawing Sheets

(56) References Cited

U.S. PATENT DOCUMENTS

| | | | |
|---|---|---|---|
| 7,016,023 B2 | 3/2006 | Peerlings | |
| 7,197,242 B2 | 3/2007 | Sasaoka | |
| 7,239,442 B2 | 7/2007 | Kourogi et al. | |
| 7,551,342 B2 | 6/2009 | Kourogi et al. | |
| 7,712,977 B2 | 5/2010 | Kourogi et al. | |
| 7,769,298 B2 | 8/2010 | Igarashi et al. | |
| 7,881,620 B2 | 2/2011 | Nicholson et al. | |
| 8,023,775 B2 | 9/2011 | Sakamoto et al. | |
| 8,120,841 B2 | 2/2012 | Sosabowski et al. | |
| 8,135,275 B2 | 3/2012 | Heismann et al. | |
| 8,175,464 B2 | 5/2012 | Eiselt et al. | |
| 8,447,155 B1 | 5/2013 | Kuo et al. | |
| 8,482,847 B2 | 7/2013 | Kuo et al. | |
| 8,571,075 B2 | 10/2013 | Fermann et al. | |
| 8,571,419 B2 | 10/2013 | Bouda | |
| 8,611,759 B1 | 12/2013 | Kvavle et al. | |
| 2002/0159119 A1 | 10/2002 | Fries et al. | |
| 2004/0208607 A1 | 10/2004 | Eiselt et al. | |
| 2006/0109452 A1 | 5/2006 | Loecklin | |
| 2008/0285606 A1* | 11/2008 | Kippenberg et al. | 372/32 |
| 2010/0284431 A1 | 11/2010 | Inoue | |
| 2012/0087004 A1 | 4/2012 | Kwon et al. | |
| 2013/0229662 A1* | 9/2013 | Ogawa | 356/453 |
| 2014/0254619 A1 | 9/2014 | Ataie et al. | |
| 2015/0029575 A1 | 1/2015 | Hara et al. | |

OTHER PUBLICATIONS

Theodor W Hansch, Laser Spectroscopy and Frequency Combs, Jan. 1, 2013, Journal of Physics: Conference Series, pp. 1-17.*

Birgitta Bernhardt, Cavity-enhanced dual-comb spectroscopy, Nov. 29, 2009, Nature Photonics, pp. 1-10.*

Christoph Gohle, Frequency Comb Vernier Spectroscopy for Broadband, High-Resolution, High-Sensitivity Absorption and Dispersion Spectra, Dec. 31, 2007, Physical Review Letters, pp. 1-4.*

Hao Chi, Fiber chromatic dispersion measurement based on wavelength-to-time mapping using a femtosecond pulse laser and an optical comb filter, Dec. 2007, Optics Communications, vol. 280, pp. 337-342.*

Kuo, B.P.-P. et al., "Highly nonlinear fiber with dispersive characteristic invariant to fabrication fluctuations", Opt Express. Mar. 26, 2012;20(7); pp. 7716-7725.

Radic, S., Parametric Signal Processing, IEEE Journal of Selected Topics in Quantum Electronics, vol. 18, No. 2, Mar./Apr. 2012, pp. 670-680.

Kuo, B. P. P., et al. "Transmission of 640-Gb/s RZ-OOK Channel over 100-km SSMF by wavelength-transparent conjugation," J. Lightwave Technol. 29, pp. 516-523 (2011).

Kuo, B. P. P., et al. "Simultaneous wavelength-swept generation in NIR and SWIR bands over combined 329-nm band using swept-pump fiber optical parametric oscillator," J. Lightwave Technol. 29, pp. 410-416 (2011).

Wiberg, A.O.J., et al., "Coherent Filterless Wideband Microwave/Millimeter-wave Channelizer based on Broadband Parametric Mixers", Journal of Lightwave Technology 32(20),3609-3617,2014.

Kuo, B.P.-P., et al, "Wideband Parametric Frequency Comb as Coherent Optical Carrier", J. Lightwave Tech., 31(21), Nov. 1, 2013, pp. 3414-3419.

Kelly, M., "Improving Chromatic Dispersion and PMD Measurement Accuracy", White Paper, Agilent Technologies.

Chi, H. and Yao, J., "Fiber chromatic dispersion measurement based on wavelength-to-time mapping using a femtosecond pulse laser and an optical comb filter", Optics Communications, 280 (2007) 337-342.

Myslivets, E. and Radic, S., Spatially Resolved Measurements of Chromatic Dispersion in Fibers, J. Lightwave Technology, 33(3) Feb. 1, 2015, 597-608.

Kuo, B.P.-P., et al., "Continuous-wave, short-wavelength infrared mixer using dispersion-stabilized highly-nonlinear fiber", Optics Express, 20(16), Jul. 30, 2012, 18422-18431.

Ataie, v., et al., "Ultrafast Absolute Ranging by Coherent Parametric Comb," in Optical Fiber Communication Conference, OSA Technical Digest (online) (Optical Society of America, 2013), paper OTh3D.2.

Tong, Z. et al., "Spectral linewidth preservation in parametric frequency combs seeded by dual pumps", Optics Express, 20(16) Jul. 30, 2012, 17610-17619.

Temprana, E., et al., "Low-noise parametric frequency comb for continuous C-plus-L-band 16-QAM channels generation," Opt. Express 22, 6822-6828 (2014).

* cited by examiner

COHERENT DUAL PARAMETRIC FREQUENCY COMB FOR ULTRAFAST CHROMATIC DISPERSION MEASUREMENT IN AN OPTICAL TRANSMISSION LINK

RELATED APPLICATIONS

This application claims the benefit of the priority of U.S. application No. 61/773,097, filed Mar. 5, 2013, the disclosure of which is incorporated herein by reference in its entirety.

FIELD OF THE INVENTION

The present invention relates to a device and method for ultra-fast measurement of optical chromatic dispersion through the coherent multi-heterodyne detection of two broad band optical frequency combs.

BACKGROUND OF THE INVENTION

Chromatic dispersion involves the spreading of an optical signal due to the wavelength dependence of the velocity of propagation of the optical signal. If an optical signal contains multiple wavelengths, chromatic dispersion can cause the constituent wavelengths of the optical signal to travel at different speeds through the optical fiber so that they arrive at different times at the receiver, resulting in a "spreading" of the optical signal. Chromatic dispersion may occur as a result of the materials within the optical fibers and/or geometries of the optical fibers.

Excessive amounts of accumulated dispersion in high-speed optical communication systems can severely degrade the quality of the transmitted signals. The effect of accumulated dispersion is particularly important in communication systems that transmit signals over long spans of standard single-mode fibers, which may exhibit chromatic dispersion of up to 17 ps/nm/km. To reduce the resulting signal degradation, the chromatic dispersion in the fiber link is often compensated for using dispersion-compensating modules that are interspersed with the fiber spans and designed to substantially reduce the accumulated total chromatic dispersion in each fiber span. However, the exact amount of accumulated dispersion, which transmitted signals experience in the fiber spans and dispersion-compensating modules in a given link, is often unknown because the fiber link was originally designed to transmit signals at substantially lower data rates, which are more tolerant to residual accumulated chromatic dispersion. Therefore, in order to assess whether a certain transmission link can be upgraded to transmit signals at higher data rates, the overall accumulated chromatic dispersion of the fiber link must be re-measured.

In general, chromatic dispersion measurement can be classified into the categories of time-of-fight (TOF), modular phase shift (MPS), and optical-interferometry based methods. (See, H. Chi and J. Yao, "Fiber chromatic dispersion measurement based on wavelength-to-time mapping using a femtosecond pulse laser and an optical comb filter", *Optics Communications* 280 (2007) 337-342, which is incorporated herein by reference.)

The chromatic dispersion can be measured either individually for each fiber span and dispersion-compensating module or, alternatively, in a single end-to-end measurement. Most existing dispersion measurement devices utilize a single frequency tunable laser and require a single measurement for each measurement frequency step.

BRIEF SUMMARY

The invention relies on wide-band optical frequency comb to estimate the optical phase shift induced in the dispersive material. In contrast to the conventional techniques that rely on a single tunable laser for extracting the dispersion parameter at different frequencies, the present invention uses multiple comb lines for simultaneously evaluating the dispersion induced phase shifts in different frequencies. Since the frequency response of the dispersive material is merely a phase function, a phase associated with each comb line passed through the material (denote as "received" hereinafter) represents a discrete measure of the material frequency response.

In one embodiment, a method for measurement of chromatic dispersion in an optical material comprises using a wide-band optical frequency comb to estimate an optical phase shift induced in the optical material.

In another embodiment, a device for measurement of chromatic dispersion in an optical material comprises a laser source; a dual-phase locked optical frequency comb for receiving an optical signal from the laser source and providing an input into a first end of the optical material, the input comprising a plurality of comb lines; a detector at a second end of the optical material for converting received optical comb lines into electrical comb lines; and a processor for determining a phase shift in the electrical comb lines.

In a further embodiment, a method for calculating chromatic dispersion in an optical material comprises collecting target paths and calibrator paths for a single cycle of a received frequency comb spacing mismatch; extracting phase information of frequency points; and determining a dispersion profile from the extracted frequency points.

BRIEF DESCRIPTION OF THE DRAWINGS

The present invention will be better understood from the following detailed description of some preferred embodiments of the invention, taken in conjunction with the accompanying drawings, in which like numbers correspond to like parts, and in which.

DETAILED DESCRIPTION

According to the invention, a wide-band optical frequency comb is employed to estimate the optical phase shift induced in an optical transmission medium. The examples described herein involve an optical fiber as the transmission medium, however, "transmission medium" may be an optical system and or device that includes or interfaces with an optical fiber, or any medium in which optical transmission can occur, including air, water or other liquid, or other materials.

Figure 1:
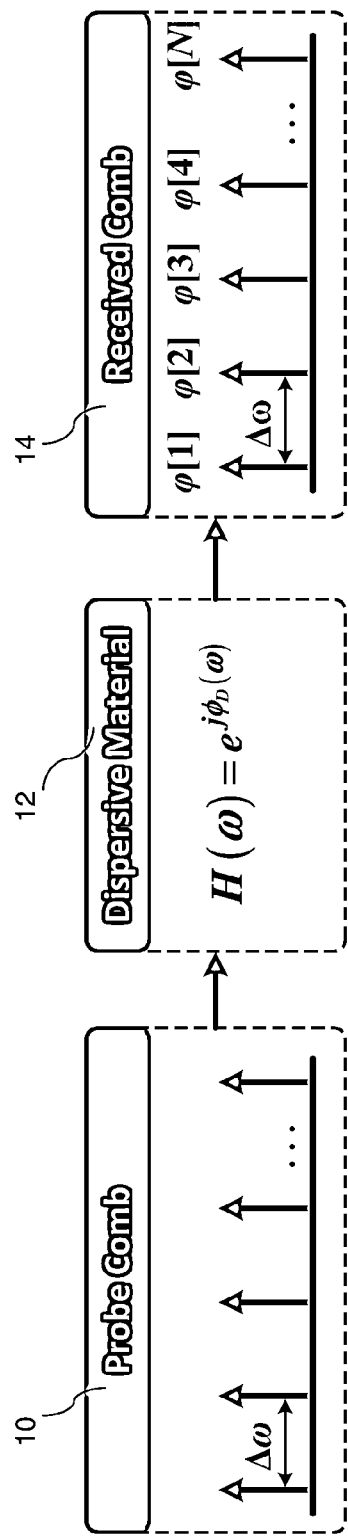
FIG. 1 illustrates a dispersion measurement architecture using frequency comb.

The basic architecture of the invention is illustrated in FIG. 1. In particular, multiple comb lines 10 are used at the same time for evaluating the dispersion-induced phase shifts in different frequencies caused by a dispersive material 12. Since the frequency response of the dispersive material is merely a phase function, a phase associated with each comb line 14 passed through the material (denoted as the "Received Comb") represents a discrete measure of the material frequency response.

The Received Comb 14 can be expressed as a product of the delta Dirac train and material frequency response. Consequently, the phase of the each received comb line ([1], [2], [3], [4], . . . [N]) can be expressed as:

$$\Phi[n] = \Phi(\omega)|_{\omega = n\Delta\omega,\ k=1,2,3,\ldots} = \Phi_L(\omega) + \Phi_D(\omega)|_{\omega = n\Delta\omega,\ k=1,2,3,\ldots} \quad (1)$$

Where, $\Phi_L(\omega)$ is the linear phase shift induced by propagation in the medium, and $\Phi_D(\omega)$ is the phase shift associated with chromatic dispersion. For Eq. (1) to be valid, all comb lines from Probe Comb 10 must carry the same initial phase. Once the phases of the received comb lines in Received Comb 14 are estimated, the group delay and dispersion can be evaluated using the following relationships:

$$\tau_g(\omega) = -\frac{d\phi(\omega)}{d\omega} \quad (2)$$

$$D(\lambda) = \frac{\omega^2}{2\pi c} \frac{d\tau_g(\omega)}{d\omega}$$

Where, $\tau_g(\omega)$ is the group delay as function of frequency, C is the speed of light in the material, and $D(\omega)$ is the dispersion parameter as a function of frequency. Equivalently, the dispersion can be obtained in the discrete domain as:

$$\tau_g[n] = \tau_g(\omega)|_{\omega=n\Delta\omega, n=1,2,3,\ldots} = -\frac{\phi[n] - \phi[n-1]}{\Delta\omega}, \quad (3)$$

$$D[n] = D(\omega)|_{\omega=n\Delta\omega, n=1,2,3,\ldots} =$$

$$\frac{\omega[n]^2}{2\pi c} \frac{d\tau_g[n]}{\Delta\omega} = \frac{\omega[n]^2}{2\pi c} \frac{\phi[n] - 2\phi[n-1] + \phi[n-2]}{\Delta\omega^2}$$

Figure 2:
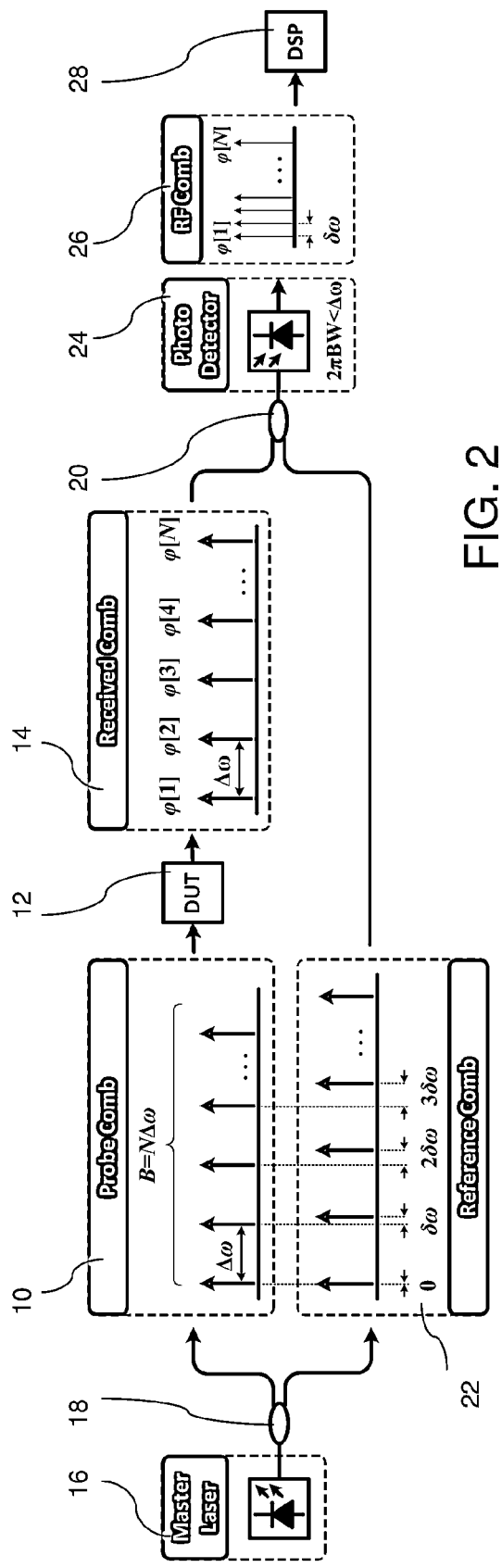
FIG. 2 illustrates a dispersion measurement topology using dual phase-locked optical frequency comb with different frequency spacing offset.

The linear phase shift due to the propagation, $\Phi_L(\omega)$, vanishes after the second derivation operation in Eq. (3), and the dispersive phase shift, $\Phi_D(\omega)$ is the only term that contributes to the dispersion calculation. Referring to FIG. 2, a second frequency comb (Reference Comb 22) with different frequency spacing offset, $\Delta\omega+\delta\omega$, can be used to coherently transfer the wide-band optical field of the Received Comb 14 to an equivalent electrical-domain signal, as shown in FIG. 2. FIG. 2 illustrates a dispersion measurement topology using a master laser 16 feeding through splitter 18 into a dual phase-locked optical frequency comb formed by Probe Comb 10 and Reference Comb 22. The two combs have different frequency spacing offsets. Propagation of the Probe Comb 10 through the dispersive material 12 (labeled "DUT" for "device under test") imposes phase shifts on the constituent comb lines. The optical field of Received Comb 14 is combined with the field from the Reference Comb 22 at combiner 20 for detection by photodetector 24. The detected signal is input into RF Comb 26, with the filtered output to a digital signal processor (DSP) 28.

Utilizing single low bandwidth ($2\pi BW<\Delta\omega$) photo diode 24 to detect the combined optical field of the Received 14 and Reference comb 22, the phase shift of each Received Comb line can be mapped to the corresponding comb line of the electrical signal, which are separated by the frequency-spacing mismatch $\delta\omega$. Consequently, the characteristic (i.e., dispersion) of the device under test (DUT) 12 can be resolved in a single cycle of spacing mismatch through a standard Fourier transform technique.

The minimum required capturing time for the inventive technique is equal to a single period of lowest harmonic of the RF comb or equivalently:

$$T_{min} = \frac{2\pi}{\delta\omega}. \quad (4)$$

In contrast, for conventional techniques, the minimum required capturing time is limited to the required laser tuning time. Considering that the laser frequency tuning time for the single point of the measurement cannot exceed the laser cavity lifetime, the minimum required capturing time can be obtained as:

$$T_{min} > \frac{\text{Number of Measurement Steps}}{\text{Laser\ Linewidth}}, \quad (5)$$

which can be easily four orders of magnitude slower than the inventive technique.

Figure 3:
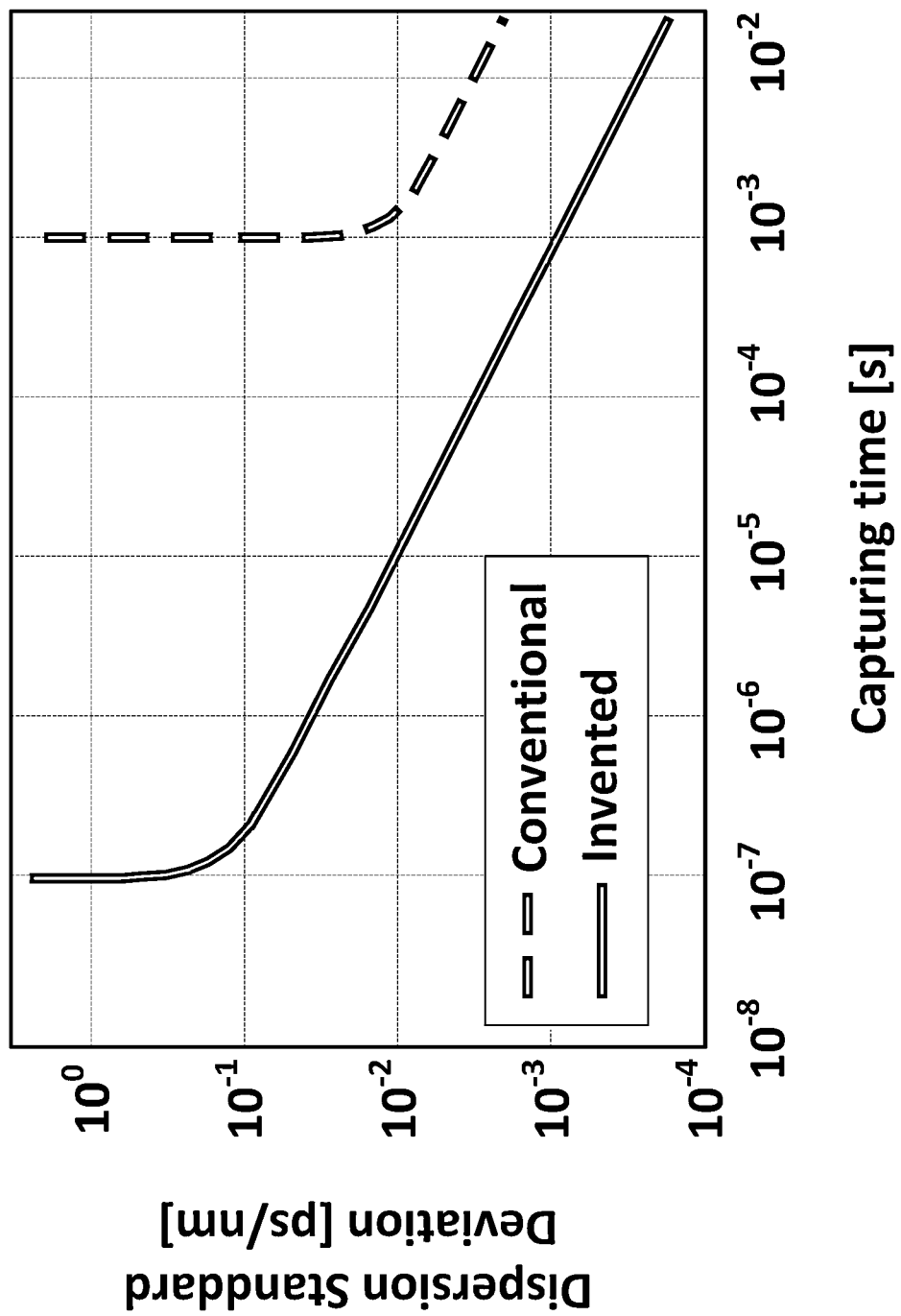
FIG. 3 shows the time/accuracy curves for the two (invented and conventional) scenarios.

FIG. 3 shows the time/accuracy curves for the two (inventive and conventional) scenarios. For comparison, a dispersion measurement was performed over a 100-nm bandwidth using a frequency comb with 100 lines and 1 nm line spacing (i.e., the present invention) and a single frequency tunable laser and 100 distinct measurements (i.e., conventional method), respectively. We assumed that the signal to noise ratio of the received signal in both scenarios was equal to 10 dB, the electrical receiver bandwidth was 1 GHz, and the laser linewidth was 100 kHz. The number of lines in the frequency comb may vary based on the desired degree of precision. As is known in the art, frequency combs may range from 10 or fewer lines to 1000 or more lines. Selection of an appropriate number of lines will be readily apparent to one of skill in the art.

For the inventive technique, the 100 number of comb lines together with the 1 GHz receiver bandwidth, requires that $\delta\omega$ be 10 MHz, which is equivalent to 100 ns minimum capturing time using the inventive technique (Eq. (4)). Beyond that point, the measurement accuracy drops as 5 dB/decade of increase in capturing time. In contrast, for the conventional technique, the minimum required capturing time for the whole 100 nm band is defined by Eq. (5), which is 1 ms. Furthermore, simultaneous capturing and processing of the 100 lines, benefits the invention to be 100 times faster while achieving the same measurement accuracy.

FIG. 3 is a plot of dispersion measurement accuracy as a function of capturing time. The signal to noise ratio of the received signal was 10 dB, the receiver bandwidth was 1 GHz, the comb consisted of 100 lines with 1 nm line spacing, and the laser linewidth assumed to be 100 KHz (laser frequency tuning time >100×10 μs).

Figure 4:
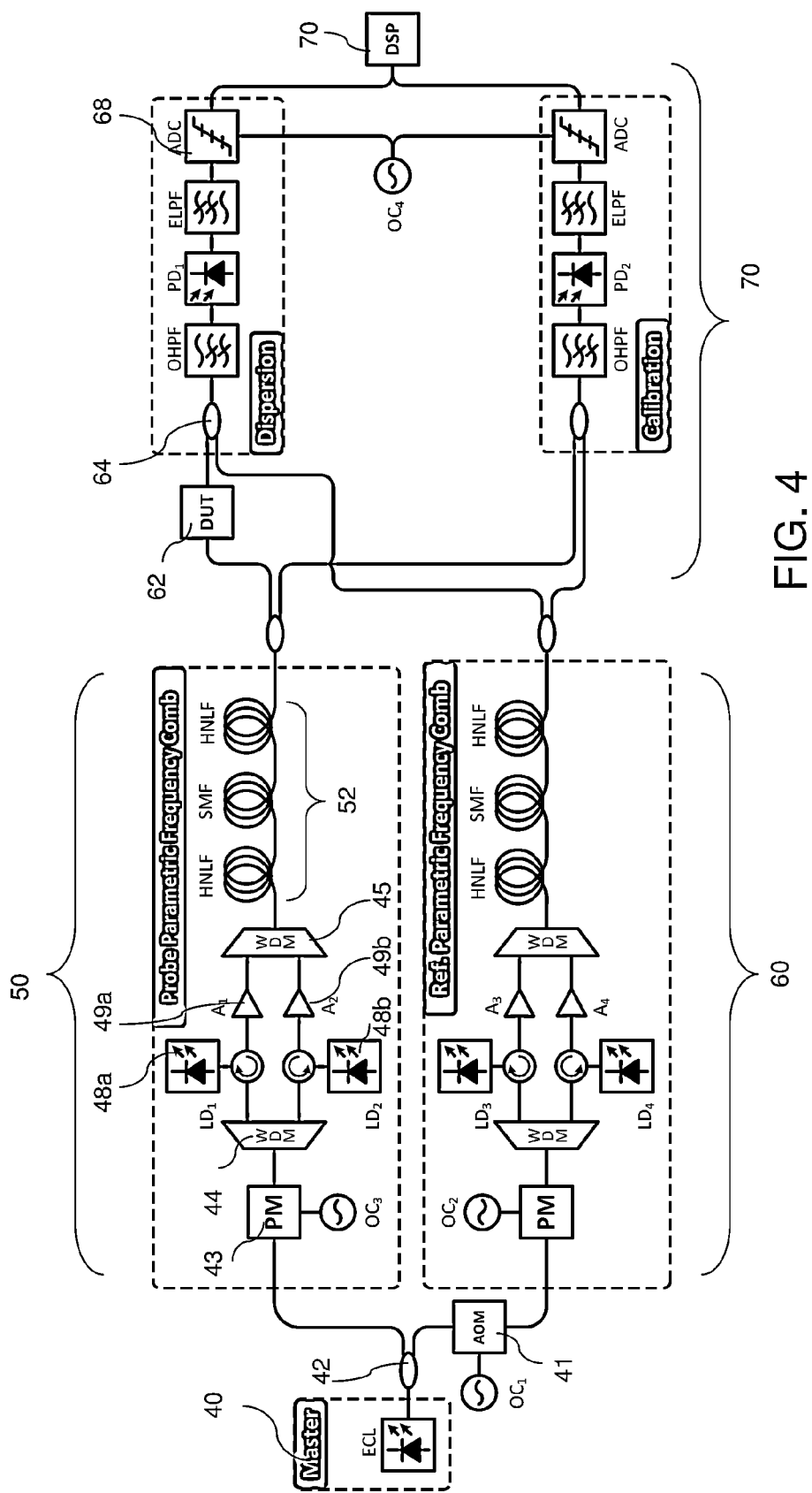
FIG. 4 shows an exemplary proposed experimental setup for the inventive dispersion measurement technique.

FIG. 4 illustrates an exemplary experimental setup for the inventive dispersion measurement technique. The illustrated elements include ECL: external cavity laser, AOM: acousto-optic modulator, OC: oscillator, LD: laser diode, PM: phase modulator, A: amplifier, WDM: wavelength division multiplex filters, HNLF: highly nonlinear fiber, SMF: single mode fiber, OHPF: optical filter, PD: photodiode, ADC: analog-to-digital converter, DSP: digital signal processor, DUT: device under test.

The master tone for phase-locking of the probe and reference comb was provided by an external cavity laser (ECL) 40 which was split into two paths at splitter 42, and subsequently amplified and phase modulated to create the phase-locking reference for the probe and reference frequency combs. To generate the phase-locked probe comb 50, the master laser tone from laser 40 was phase-modulated (phase modulator 43a) at 25 GHz to span a 5-nm wide comb comprising 25-GHz harmonics up to the eighth-order. The second-order harmonics in both the upper and lower sidebands were extracted from the master laser comb by wavelength division multiplex (WDM) filter 44 and injected into two distributed feedback lasers ($LD_1$(48a), $LD_2$(48b)) to create a pair of pump tones separated by 100 GHz through injection locking. The pump tones, both possessing shot-noise limited signal-to-noise ratios (SNR), were amplified (amplifiers 49a and 49b) to 500 mW individually and combined at WDM filter 45 to drive a parametric mixer for wide-band optical frequency comb generation. The parametric mixer consisted of multiple nonlinear and linear fiber sections (52) with dispersion and Brillouin scattering managed by longitudinal strain, which enabled generation of a 100-nm wide optical frequency comb. On the other side, the reference comb 60 was generated using a similar set of apparatus as for the probe comb 50, except the incoming master laser tone was frequency-shifted using an acousto-optical modulator (AOM) 41, and the phase-modulation frequency was offset from 25 GHz by 2.5 MHz in order to increase the comb frequency spacing by 10 MHz. These frequency offsets ensured a progressive frequency walk-off between the reference and probe comb at a step of 10 MHz per tone-order.

The probe frequency comb, after passing through the DUT 62, was combined with the reference comb at combiner 64 for coherent detection. The heterodyne signal was recorded by an analog-to-digital converter (ADC) 68 operating at a sampling rate of 1 GS/s. In order to suppress the influence of environmental perturbation to the measurement, a non-dispersive path was measured using an identical set of apparatus. The phase fluctuations recorded in this calibrator path 70 were subtracted by the DSP 72 from the measured target object distance in post-processing procedures.

The DUT's dispersion was calculated in DSP 70 by a three-step processing routine using the recorded samples from the ADCs. In the first step, the samples of target and calibrator paths were accumulated for a single cycle of the frequency comb spacing mismatch (10 MHz), and underwent a fast Fourier transform (FFT) to reconstruct the instantaneous spectrum of the received frequency comb. In the second step, the phase information of the frequency points was extracted. The phases of the calibrator FFT coefficients were subtracted from the DUT coefficients in order to compensate for phase deviation due to environmental perturbation. The final step extracted the DUT dispersion profile using Eq. (3).

The inventive method can be implemented in a small package, allowing it to be conveniently deployed as a commercial dispersion measuring device. The invention provides a significant advantage over prior art systems, measuring dispersion over ~100 nm of bandwidth with a single shot measurement, enabling accuracy that is 100 times better than existing systems that rely on time averaging.

What is claimed is:

1. A method for evaluating an optical transmission link for spreading of an optical signal across a length of the link, comprising:
   measuring the optical transmission link for the presence of chromatic dispersion across the length of the link using a wide-band optical frequency comb having a plurality of comb lines to estimate optical phase shifts simultaneously at a plurality of different frequencies;
   wherein measuring the optical transmission link further comprises mapping the estimated optical phase shift of each received comb line to a corresponding comb line of an electrical signal separated by a frequency-spacing mismatch;
   setting the minimum required capturing time for measuring the optical transmission link to a single period of lowest harmonic of the reference comb; and
   estimating the chromatic dispersion in a single cycle of frequency-spacing mismatch.

2. The method of claim 1, wherein the wide-band optical frequency comb is a dual-phase locked optical frequency comb comprising a probe comb and a reference comb, wherein the probe comb and the reference comb have difference frequency offset spacings.

3. The method of claim 1, wherein the wide-band optical frequency comb comprises more than 10 lines.

4. The method of claim 1, wherein the wide-band optical frequency comb comprises approximately 100 lines with a spacing of approximately 1 nanometer (nm).

5. The method of claim 4, further comprising measuring for the presence of chromatic dispersion in 1 millisecond (ms) when an electrical receiver bandwidth is 1 gigahertz (GHz) and a laser linewidth is 100 kilohertz (kHz).

6. A system for measurement of chromatic dispersion, comprising:
   a laser source;
   an optical fiber span;
   a dual-phase locked optical frequency comb disposed at a first end of the optical fiber span and configured for receiving an optical signal from the laser source and generating an input into the first end of the optical fiber span, the input comprising a plurality of comb lines at a plurality of different frequencies for simultaneous transmission over the optical fiber span;
   a detector disposed at a second end of the optical fiber span, the detector configured for simultaneously receiving and converting received optical comb lines transmitted across a length of the optical fiber span into electrical comb lines; and
   a processor for determining a phase shift in each of the electrical comb lines;
   wherein the processor determines the phase shift by mapping an estimated optical phase shift of each comb line to a corresponding electrical comb line separated by a frequency-spacing mismatch;
   wherein the processor sets the minimum required capture time for measuring the optical transmission link to a single period of lowest harmonic of the reference comb; and
   wherein the processor estimates the chromatic dispersion in a single cycle of frequency-spacing mismatch.

7. The system of claim 6, wherein the dual-phase locked optical frequency comb comprises a probe comb and a reference comb, and wherein the probe comb and the reference comb have difference frequency offset spacings.

8. The system of claim 6, wherein the dual-phase locked optical frequency comb comprises more than 10 lines.

9. The system of claim 6, wherein the dual-phase locked optical frequency comb comprises approximately 100 lines with a spacing of approximately 1 nanometer (nm).

10. The system of claim 9, wherein a minimum required capturing time for measurement of the presence of chromatic dispersion is 1 millisecond (ms) with an electrical receiver bandwidth of 1 gigahertz (GHz) and a laser linewidth of 100 kilohertz (kHz).

11. The system of claim 6, wherein the plurality of comb lines are configured to estimate optical phase shifts at different frequencies at the same time.

12. A method for optimizing an optical transmission link, comprising:
   evaluating an optical transmission link for upgrading to higher data rate transmission by measuring chromatic dispersion within the optical transmission link using an optical frequency comb having from 10 to 100 comb lines to estimate optical shifts simultaneously at a plurality of different frequencies;
   wherein the wide-band optical frequency comb is a dual-phase locked optical frequency comb comprising a probe comb and a reference comb, wherein the probe comb and the reference comb have difference frequency offset spacings;
   setting the minimum required capturing time for measuring the optical transmission link to a single period of lowest harmonic of the reference comb; and
   estimating the chromatic dispersion in a single cycle of frequency-spacing mismatch.

13. The method of claim 12, wherein the wide-band optical frequency comb comprises approximately 100 lines with a spacing of approximately 1 nanometer (nm).

* * * * *